United States Patent [19]

Bugaut et al.

[11] 4,323,360
[45] Apr. 6, 1982

[54] DYEING COMPOSITIONS FOR HAIR WHICH CONTAIN 2,4-DIAMINO-BUTOXYBENZENE AND/OR A SALT THEREOF AS THE COUPLING AGENT

[75] Inventors: Andree Bugaut, Boulogne; Alex Junino, Aulnay-sous-Bois, both of France

[73] Assignee: L'Oreal, Paris, France

[21] Appl. No.: 159,920

[22] Filed: Jun. 16, 1980

[30] Foreign Application Priority Data

Jun. 18, 1979 [FR] France ................................ 79 15553

[51] Int. Cl.$^3$ ............................................... A61K 7/13
[52] U.S. Cl. ............................................. 8/407; 8/408; 8/409; 8/410; 8/411; 8/412; 8/416; 8/406
[58] Field of Search ................... 8/408, 407, 416, 411, 8/406, 409, 410, 412

[56] References Cited

U.S. PATENT DOCUMENTS

| | | | |
|---|---|---|---|
| 1,144,325 | 6/1915 | Erlenbach | 8/411 |
| 4,125,367 | 11/1978 | Bugaut et al. | 8/407 |
| 4,171,203 | 10/1979 | Rose et al. | 8/416 |
| 4,226,595 | 10/1980 | Rose et al. | 8/408 |

Primary Examiner—Donald B. Moyer

[57] ABSTRACT

An oxidation hair dye composition is provided which comprises, as coupling agent, 2,4-diamino-butoxybenzene or a salt thereof.

35 Claims, No Drawings

DYEING COMPOSITIONS FOR HAIR WHICH CONTAIN 2,4-DIAMINO-BUTOXYBENZENE AND/OR A SALT THEREOF AS THE COUPLING AGENT

DESCRIPTION

The importance of meta-phenylenediamines in so-called oxidation dyeing of hair is well-known. This importance is due to the fact that these coupling agents can serve as precursors of blue, orange or red dyes, depending on whether they are combined, in an alkaline oxidizing medium, with para-phenylenediamines or with para-aminophenols.

In fact, in combination with para-phenylenediamines, in an alkaline oxidizing medium, principally in an ammoniacal medium in the presence of hydrogen peroxide, the meta-phenylenediamines give indamines, which impart shades ranging from green-blue to purple-blue to the hair. On the other hand, in combination with para-aminophenols in an alkaline oxidizing medium, they give indo-anilines, which impart shades ranging from orange to red to the hair.

The introduction of the meta-phenylenediamines into the so-called oxidation dyeing compositions for hair, that is to say the introduction of compounds which can act as precursors both for blue dyes and for orange or red dyes, if they are combined simultaneously with para-phenylenediamines and with para-aminophenols, makes it possible to formulate a whole range of dyeing compositions for natural shades, namely blacks, greys, browns or chestnuts which are of varying depth and ashen or golden. However, while the meta-phenylenediamines are of great interest as a result of the shades which they can provide in oxidation dyeing of hair, they must, like all the dye precursors used in this field, on the one hand lead to colorations having good stability to light, to the weather, to shampooing and to perspiration and, on the other hand, be very safe to use.

The present invention involves the introduction, into the oxidation dyeing compositions, of a meta-phenylenediamine not previously used for this purpose, namely 2,4-diamino-butoxybenzene, of the formula:

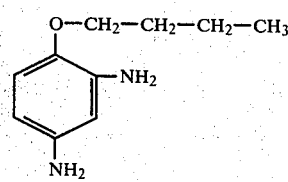

or a corresponding salt such as the hydrochloride, sulphate, citrate and lactate.

The compound of formula (I) and its salts give shades which exhibit all the high stability characteristics enumerated above and additionally have the advantage of being very safe.

The use of 2,4-diaminoanisole has been known for a long time, but this product, though possessing good dyeing properties, has the disadvantage of being highly mutagenic in the Ames test (see, for example, Ames "The detection of chemical mutagens with enteric bacteria in a Hollander", Chemical Mutagens, Principles and Methods for their detection, Vol. 1, Phenum Press, New York, 1971, pp 267–282 and Ames, McCann and Yamasaki, "Methods of detecting carcinogens and mutagens with Salmonella/mamammalian microsome mutagenicity test" Mutation Research, 31, 1975 pp 347–364.) on Salmonella typhimurium (TA 1538, TA 98, in the presence of "S9 mix" activated with "Aroclor 1254"). 2,4-Diaminoethoxybenzene is also highly mutagenic. The corresponding propoxy and isopropoxy derivatives exhibit a mutagenic effect which is still substantial, though less marked. In contrast, 2,4-diaminobutoxybenzene is, surprisingly and unexpectedly, not mutagenic in the Ames test on Salmonella typhimurium in the presence of "S9 mix" activated with "Aroclor 1254".

Accordingly, the present invention provides a dyeing composition for hair, containing 2,4-diaminobutoxybenzene or at least one of its salts in combination with at least one oxidation base, this composition being intended to be used in the presence of an oxidizing agent, preferably hydrogen peroxide. The compound of the formula (I), or one of its salts, is generally used in the compositions according to the invention at concentrations of 0.005 to 2.5% by weight relative to the total weight of the composition.

In a preferred embodiment of the invention, the dyeing composition of this invention only contains non-mutagenic oxidation bases and non-mutagenic coupling agents as the oxidation bases and as the coupling agents respectively.

The non-mutagenic oxidation bases used in the compositions according to the invention are advantageously selected from the following:

(a) the para-phenylenediamines and especially para-phenylenediamine, 2,6-dimethyl-para-phenylenediamine, 2,3-dimethyl-para-phenylenediamine, 2,6-dimethyl-3-methoxy-para-phenylenediamine, n-β-methoxyethyl-para-phenylenediamine, N,N-di-β-hydroxyethyl-para-phenylenediamine, N-ethyl-N-β-hydroxyethyl-para-phenylenediamine, N-ethyl-N-carbamylmethyl-para-phenylenediamine, N-ethyl-N-β-mesylaminoethyl-para-phenylenediamine and N-β-hydroxyethyl-N-β-mesylaminoethyl-para-phenylenediamine;

(b) the heterocyclic bases and especially 2,5-diaminopyridine, and (c) the substituted or unsubstituted paraaminophenols, and especially para-aminophenol, 2-methyl-para-aminophenol and 3-methyl-para-aminophenol.

As a coupling agent or as coupling agents, the dyeing composition according to the invention may contain, in addition to the compound of the formula (I) or at least one of its salts, at least one nonmutagenic coupling agent selected from the following:

(a) meta-phenylenediamines and especially 2,4-diamino-phenoxyethanol, 2,4-diamino-phenyl β-mesylaminoethyl ether, (2-N-carbamylmethylamino-4-amino-phenoxy)-ethanol, 2-N-β-hydroxyethylamino-4-amino-phenyl β-methoxyethyl ether, (2-N-β-hydroxyethylamino-4-amino-phenoxy)ethanol, 2-N-β-hydroxyethylamino-4-amino-phenyl β-mesylaminoethyl ether and 2,4-diaminophenyl β-aminoethyl ether;

(b) meta-aminophenols, and especially meta-aminophenol, 2-methyl-5-amino-phenol, 2-methyl-5-N-β-hydroxyethylamino-phenol, 2-methyl-5-N-β-mesylaminoethylamino-phenol, 2-methyl-5-N-carbamylmethylaminophenol, 3-N-carbamylmethylaminophenol and 2,6-dimethyl-3-acetylamino-phenol;

(c) meta-diphenols and especially resorcinol and 2-methyl-resorcinol and (d) 6-hydroxy-benzomorpholine, α-naphthol, 1-phenyl-3-methyl-pyrazol-5-one and 6-aminobenzomorpholine.

In addition to the oxidation bases and the coupling agents mentioned above, the dyeing compositions according to the invention can contain ortho-aminophenol and pyrocatechol, which are non-mutagenic products and which, in an oxidizing medium, react by more complex mechanisms with the para-phenylenediamines.

In addition, the dyeing compositions according to the invention can contain 1,2,4-trihydroxybenzene and 2,4,5-trihydroxytoluene.

The compositions according to the invention can also contain at least one direct dye which is non-mutagenic or very slightly mutagenic such as ortho-nitroaniline, 2-amino-3-nitro-isopropylbenzene, 3-nitro-4-aminophenol, 3-nitro-4-N-β-hydroxyethylamino-phenol, 2-methyl-4-amino-5-nitro-phenol, 2-nitro-4-methyl-6-amino-phenol, 3-nitro-6-N-β-hydroxyethylamino-anisole, 2-amino-3-nitro-phenol, (3-N-methylamino-4-nitro-phenoxy)-ethanol, (2-N-β-hydroxyethylamino-5-nitro-phenoxy)-ethanol, 3-nitro-4-N'-methylamino-N,N-di-β-hydroxyethyl-aniline, 3-nitro-4-N'-β-hydroxyethylamino-N,N-di-β-hydroxyethyl-aniline and 3-nitro-4-N'-methylamino-N-methyl-N-β-hydroxyethyl-aniline.

Advantageously, the composition according to the invention contains 0.002 to 2.5% by weight of direct dye or dyes, relative to the total weight of the composition.

The pH of the dyeing compositions according to the invention is basic for example from 8 to 11.5. Among alkalizing agents which can be used to provide this pH, there may be mentioned ammonia, the alkylamines, such as ethylamine or triethylamine, the alkanolamines, such as monoethanolamine, diethanolamine or triethanolamine, the alkyl-alkanolamines, such as methyldiethanolamine, sodium hydroxide, potassium hydroxide, sodium carbonate, potassium carbonate and ammonium carbonate. Among acidifying agents which can be used, there may be mentioned lactic acid, acetic acid, tartaric acid and phosphoric acid.

Water-soluble anionic, cationic, non-ionic or amphoteric surface-active agents can be added to the composition according to the invention. Among the particularly useful surface-active agents, there may be mentioned the alkylbenzenesulphonates, the alkyl-naphthalenesulphonates, the fatty alcohol sulphates, ether-sulphates and sulphonates, the quaternary ammonium salts such as trimethylcetylammonium bromide and cetylpyridinium bromide, the diethanolamides of fatty acids, polyoxyethyleneated and polyglycerolated acids and alcohols, and polyoxyethyleneated and polyglycerolated alkylphenols. Preferably, the surface-active products are present in the composition according to the invention in an amount from 0.5 to 50% by weight and advantageously 4 to 40% by weight relative to the total weight of the composition.

It is also possible to add to the compositions according to the invention organic solvents for solubilizing compounds which would be insufficiently soluble in water. Among the solvents which can advantageously be used there may be mentioned, by way of example, ethanol, isopropanol, glycerol, glycols and their ethers such as ethylene glycol monobutyl ether, ethylene glycol, propylene glycol, diethylene glycol monoethyl ether and diethylene glycol monomethyl ether. The solvents are advantageously present in the composition in an amount from 1 to 40% by weight and preferably from 5 to 30% by weight, relative to the total weight of the composition.

The compositions according to the invention can also contain thickeners, in particular sodium alginate, gum arabic, cellulose derivatives such as methylcellulose, hydroxyethylcellulose, hydroxypropylmethylcellulose and the sodium salt of carboxymethylcellulose, and polymers of acrylic acid; it is also possible to use inorganic thickeners such as bentonite. Preferably, the thickeners are present in an amount from 0.5 to 5%, and advantageously from 0.5 to 3% by weight, relative to the total weight of the composition.

The compositions according to the invention can also contain antioxidants, in particular sodium sulphite, thioglycolic acid, sodium bisulphite, ascorbic acid and hydroquinone. These antioxidants are suitably present in the composition in an amount from 0.05 to 1.5% by weight relative to the total weight of the composition.

Finally, the compositions according to the invention can contain various other adjuvants such as penetrating agents, foaming agents, sequestering agents, film-forming products and perfumes.

The composition according to the invention is generally mixed, at the time of use, with a sufficient amount of an oxidizing agent to develop the color on the keratin fibres. The oxidizing agents are preferably hydrogen peroxide, per-salts or urea peroxide.

The dyeing composition according to the invention is suitably in the form of a liquid, a cream, a gel, an aerosol or any other form which is appropriate for carrying out a hair dyeing operation.

The present invention also provides a dyeing process, in which the composition of the invention, mixed with an oxidizing agent at the time of use, is applied to the hair and after a sufficient contact time, say 5 to 45 minutes, the hair is rinsed, shampooed if appropriate, rinsed and dried.

The following Examples further illustrate the present invention. Since the compound of formula (I) and its salts are known chemical compounds no synthesis example is given.

EXAMPLE 1

The following dyeing composition is prepared:

| | |
|---|---|
| 2,4-diamino-butoxybenzene dihydrochloride | 0.5 g |
| para-aminophenol | 0.135 g |
| the sodium salt of the sulphuric acid half-ester of lauryl alcohol oxyethyleneated with two mols of ethylene oxide | 20 g |
| ethylenediaminetetraacetic acid | 0.2 g |
| sodium bisulphite (aqueous solution, of 35° B strength) | 1 g |
| ammonia (of 22° B strength) | 10 g |
| water q.s. | 100 g |

The pH of the composition is 10.5.

At the time of use, 100 g of 20 volumes strength hydrogen peroxide are added.

This mixture, when applied for 25 minutes at 28° C. to hair which has been bleached white, imparts to the hair, after rinsing and shampooing, a light red coloration.

EXAMPLE 2

The following dyeing composition is prepared:

| | |
|---|---|
| 2,4-diamino-butoxybenzene dihydrochloride | 0.46 g |
| 2,6-dimethyl-3-methoxy-paraphenylenediamine dihydrochloride | 0.43 g |
| crosslinked polyacrylic acid sold under the name "CARBOPOL 934" | 1.5 g |
| ethanol (of 96° strength) | 11 g |
| 2-butoxy-ethanol | 5 g |
| trimethylcetylammonium bromide | 1 g |
| ethylenediaminetetraacetic acid | 0.1 g |
| ammonia (of 22° B strength) | 10 g |
| thioglycolic acid | 0.2 g |
| water q.s.p. | 100 g |

The pH of the composition is 10.2.

At the time of use, 100 g of 20 volumes strength hydrogen peroxide are added.

This mixture, when applied for 30 minutes at 25° C. to hair which is naturally 90% white, imparts to the hair, after rinsing and shampooing, a silvery forget-me-not blue coloration.

EXAMPLE 3

The following dyeing composition is prepared:

| | |
|---|---|
| 2,4-diamino-butoxybenzene dihydrochloride | 0.239 g |
| 2-N-$\beta$-hydroxyethylamino-4-amino-phenyl $\beta$-mesylaminoethyl ether | 0.289 g |
| 2-methyl-5-N-carbamylmethylamino-phenol | 0.123 g |
| 3-N-carbamylmethylamino-phenol | 0.083 g |
| N-ethyl-N-$\beta$-hydroxyethyl-para-phenylenediamine dihydrochloride | 2.69 g |
| para-aminophenol | 0.54 g |
| ortho-aminophenol | 0.436 g |
| 3-nitro-6-N-$\beta$-hydroxyethylamino-anisole | 0.08 g |
| oleyl alcohol oxyethyleneated with two mols of ethylene oxide (per mol of alcohol) | 4.5 g |
| oleyl alcohol oxyethyleneated with four mols of ethylene oxide | 4.5 g |
| oleylamine oxyethyleneated with twelve mols of ethylene oxide and sold by "ARMOUR" under the name "ETHOMEEN T012" | 4.5 g |
| diethanolamides of copra fatty acids | 9 g |
| propylene glycol | 4 g |
| 2-butoxyethanol | 8 g |
| ethanol (of 96° strength) | 6 g |
| pentasodium salt of diethylenetriaminepentaacetic acid | 2 g |
| hydroquinone | 0.15 g |
| sodium bisulphite (aqueous solution of 35° B strength) | 1.3 g |
| ammonia (of 22° B strength) | 6 g |
| water q.s.p. | 100 g |

The pH of the composition is 9.2.

At the time of use, 100 g of 20 volumes strength hydrogen peroxide are added.

This mixture, when applied for 30 minutes at 30° C. to hair which has been bleached white, imparts to the hair, after rinsing and shampooing, a very deep navy blue coloration.

EXAMPLE 4

The following dyeing composition is prepared:

| | |
|---|---|
| 2,4-diamino-butoxybenzene dihydrochloride | 1.51 g |
| 2,4-diamino-phenoxyethanol dihydrochloride | 0.25 g |
| para-phenylenediamine | 1 g |
| N-ethyl-N-mesylaminoethyl-para-phenylenediamine dihydrochloride | 0.33 g |
| para-aminophenol | 0.67 g |
| ortho-aminophenol | 0.33 g |
| resorcinol | 0.89 g |
| oleyl alcohol oxyethyleneated with two mols of ethylene oxide | 4.5 g |
| oleyl alcohol oxyethyleneated with four mols of ethylene oxide | 4.5 g |
| oleylamine oxyethyleneated with twelve mols of ethylene oxide and sold by "ARMOUR" under the name "ETHOMEEN T012" | 4.5 g |
| diethanolamides of copra fatty acids | 9 g |
| propylene glycol | 4 g |
| 2-butoxy-ethanol | 8 g |
| ethanol (of 96° strength) | 6 g |
| pentasodium salt of diethylenetriaminepentaacetic acid | 2 g |
| thioglycolic acid | 0.5 g |
| ammonia (of > B strength) | 4.1 g |
| water q.s.p. | 100 g |

The pH of the composition is 9.1.

At the time of use, 100 g of 20 volumes strength hydrogen peroxide are added.

This mixture, when applied for 30 minutes at 27° C. to hair which has been bleached straw yellow, imparts to the hair, after rinsing and shampooing, a raven-black coloration with a violet sheen.

EXAMPLE 5

The following dyeing composition is prepared:

| | |
|---|---|
| 2,4-diamino-butoxybenzene dihydrochloride | 0.22 g |
| N-ethyl-N-carbamylmethyl-para-phenylenediamine | 0.93 g |
| para-aminophenol | 0.42 g |
| 2-methyl-5-N-$\beta$-hydroxyethylamino-phenol | 0.24 g |
| 6-hydroxy-benzomorpholine | 0.072 g |
| 1-phenyl-3-methylpyrazol-5-one | 0.29 g |
| carboxymethylcellulose | 2 g |
| ammonium lauryl-sulphate | 5 g |
| ammonium acetate | 1 g |
| propylene glycol | 8 g |
| pentasodium salt of diethylenetriaminepentaacetic acid | 2 g |
| thioglycolic acid | 0.4 g |
| hydroquinone | 0.15 g |
| ammonia (of 22° B strength) | 5 g |
| water q.s.p. | 100 g |

The pH of the composition is 9.6.

At the time of use, 60 g of 20 volumes strength hydrogen peroxide are added.

This mixture, when applied for 30 minutes at 25° C. to hair which is naturally 90% white, imparts to the hair, after rinsing and shampooing, a pearlescent ashen beige coloration.

EXAMPLE 6

The following dye composition is prepared:

| | |
|---|---|
| 2,4-diamino-butoxybenzene dihydrochloride | 0.015 g |
| N,N-di-$\beta$-hydroxyethyl-para-phenylenediamine dihydrochloride | 0.6 g |
| resorcinol | 0.047 g |
| meta-aminophenol | 0.035 g |
| ortho-aminophenol | 0.05 g |
| 2-methyl-5-amino-phenol | 0.041 g |
| 2-nitro-3-amino-phenol | 0.01 g |
| 2-nitro-3-N-$\beta$-hydroxyethylamino-phenol | 0.01 g |
| oleyl alcohol oxyethyleneated with two mols of ethylene oxide | 4.5 g |
| oleyl alcohol oxyethyleneated with four mols of ethylene oxide | 4.5 g |
| oleylamine oxyethyleneated with twelve mols of ethylene oxide and sold by "ARMOUR" under the name "ETHOMEEN T012" | 4.5 g |
| diethanolamides of copra fatty acids | 9 g |
| propylene glycol | 4 g |

-continued

| | |
|---|---|
| 2-butoxy-ethanol | 8 g |
| ethanol (of 96° strength) | 6 g |
| pentasodium salt of diethylenetriaminepenta-acetic acid | 2 g |
| thioglycolic acid | 0.5 g |
| ammonia (of 22° B strength) | 10 g |
| water q.s.p. | 100 g |

The pH of the composition is 10.4.

At the time of use, 80 g of 20 volumes strength hydrogen peroxide are added.

This mixture, when applied for 25 minutes at 30° C. to bleached hair, imparts to the hair, after rinsing and shampooing, a silvery mauve-grey coloration.

EXAMPLE 7

The following dyeing composition is prepared:

| | |
|---|---|
| 2,4-diamino-butoxybenzene dihydrochloride | 1.275 g |
| 2,5-diamino-pyridine dihydrochloride | 1.456 g |
| pyrocatechol | 0.11 g |
| resorcinol | 0.11 g |
| 2-methyl-resorcinol | 0.062 g |
| 3-nitro-4-amino-phenol | 0.2 g |
| carboxymethylcellulose | 2 g |
| ammonium lauryl-sulphate | 5 g |
| ammonium acetate | 1 g |
| propylene glycol | 8 g |
| pentasodium salt of diethylenetriamine-pentaacetic acid | 2 g |
| thioglycolic aicd | 0.4 g |
| hydroquinone | 0.15 g |
| ammonia (of 22° B strength) | 8.4 g |
| water q.s.p. | 100 g |

The pH of the composition is 9.3.

At the time of use, 100 g of 20 volumes strength hydrogen peroxide are added.

This mixture, when applied for 25 minutes at 28° C. to hair which is naturally 90% white, imparts to the hair, after rinsing and shampooing, a red coloration.

EXAMPLE 8

The following dyeing composition is prepared:

| | |
|---|---|
| 2,4-diamino-butoxybenzene dihydrochloride | 0.202 g |
| para-phenylenediamine | 0.95 g |
| para-aminophenol | 0.447 g |
| N-methyl-para-aminophenol sulphate | 0.258 g |
| resorcinol | 0.15 g |
| meta-aminophenol | 0.079 g |
| ortho-aminophenol | 0.436 g |
| nonylphenol oxyethyleneated with four mols of ethylene oxide and sold by RHONE POULENC under the name "CEMULSOL NP4" | 21 g |
| nonylphenol oxyethyleneated with nine mols of ethylene oxide and sold by RHONE POULENC under the name "CEMULSOL NP9" | 24 g |
| oleic acid | 4 g |
| 2-butoxy-ethanol | 3 g |
| ethanol (of 96° strength) | 10 g |
| pentasodium salt of diethylenetriamine-pentaacetic acid | 2.5 g |
| thioglycolic acid | 0.6 g |
| ammonia (of 22° B strength) | 10 g |
| water q.s.p. | 100 g |

The pH of the composition is 10.2.

At the time of use, 100 g of 20 volumes strength hydrogen peroxide are added.

This mixture, when applied for 25 minutes at 27° C. to hair which is naturally 90% white, imparts to the hair, after rinsing and shampooing, a golden medium chestnut coloration.

EXAMPLE 9

The following dyeing composition is prepared:

| | |
|---|---|
| 2,4-diamino-butoxybenzene dihydrochloride | 1 g |
| N-β-methoxyethyl-para-phenylenediamine dihydrochloride | 2 g |
| para-aminophenol | 0.44 g |
| resorcinol | 0.52 g |
| ortho-aminophenol | 0.5 g |
| crosslinked polyacrylic acid sold under the name "CARBOPOL 934" | 1.5 g |
| ethanol ( of 96° strength) | 11 g |
| 2-butoxy-ethanol | 5 g |
| trimethylcetylammonium bromide | 1 g |
| ethylenediaminetetraacetic acid | 0.1 g |
| ammonia (of 22° B strength) | 10 g |
| thioglycolic acid | 0.2 g |
| water q.s.p. | 100 g |

The pH of the composition is 9.8.

At the time of use, 100 g of 20 volumes strength hydrogen peroxide are added.

This mixture, when applied for 25 volumes strength hydrogen peroxide are added.

This mixture, when applied for 25 minutes at 30° C. to hair which has been bleached white, imparts to the hair, after rinsing and shampooing, a very deep black-blue coloration.

EXAMPLE 10

The following dyeing composition is prepared:

| | |
|---|---|
| 2,4-diamino-butoxybenzene dihydrochloride | 0.18 g |
| 2-N-β-hydroxyethylamino-4-amino-phenoxy-ethanol dihydrochloride | 0.20 g |
| 2,6-dimethyl-para-phenylenediamine dihydrochloride | 1.5 g |
| para-aminophenol | 0.4 g |
| N-ethyl-N-β-hydroxyethyl-para-phenylene-diamine dihydrochloride | 0.4 g |
| resorcinol | 0.4 g |
| 2-methyl-resorcinol | 0.2 g |
| 2-methyl-5-N-β-hydroxyethylamino-phenol | 0.4 g |
| ortho-aminophenol | 0.35 g |
| 2-nitro-3-amino-phenol | 1 g |
| oleyl alcohol oxyethyleneated with two mols of ethylene oxide | 4.5 g |
| oleyl alcohol oxyethyleneated with four mols of ethylene oxide | 4.5 g |
| oleylamine oxyethyleneated with twelve moles of ethylene oxide and sold by "ARMOUR" under the name "ETHOMEEN T012" | 4.5 g |
| diethanolamides of copra fatty acids | 9 g |
| propylene glycol | 4 g |
| 2-butoxy-ethanol | 8 g |
| ethanol (of 96° strength) | 6 g |
| pentasodium salt of diethylenetriamine-pentaacetic acid | 2 g |
| hydroquinone | 0.15 g |
| sodium bisulphite (aqueous solution of 35°B strength) | 1.3 g |
| ammonia (of 22° B strength) | 6 g |
| water q.s.p. | 100 g |

The pH of the composition is 9.

At the time of use, 100 g of 20 volumes strength hydrogen peroxide are added.

This mixture, when applied for 30 minutes at 30° C. to hair which is naturally 90% white, imparts to the hair, after rinsing and shampooing, a deep grey coloration with a metallic sheen.

EXAMPLE 11

The following dyeing composition is prepared:

| | |
|---|---|
| 2,4-diamino-butoxybenzene dihydrochloride | 2.5 g |
| para-phenylenediamine | 2.5 g |
| ortho-aminophenol | 1.7 g |
| 2-N-β-hydroxyethylamino-4-amino-phenyl β-methoxyethyl ether dihydrochloride | 0.2 g |
| (2-N-carbamylmethylamino-4-amino-phenoxy)-ethanol dihydrochloride | 0.2 g |
| oleyl alcohol oxyethyleneated with two mols of ethylene oxide | 4.5 g |
| oleyl alcohol oxyethyleneated with four mols of ethylene oxide | 4.5 g |
| oleylamine oxyethyleneated with twelve mols of ethylene oxide and sold by "ARMOUR" under the name "ETHOMEEN T012" | 4.5 g |
| diethanolamindes of copra fatty acids | 9 g |
| propylene glycol | 4 g |
| 2-butoxy-ethanol | 8 g |
| ethanol (of 96° strength) | 6 g |
| pentasodium salt of diethylenetriamine-pentaacetic acid | 2 g |
| hydroquinone | 1.3 g |
| sodium bisulphite (aqueous solution of 35° B strength) | 1.3 g |
| ammonia (of 22°B strength) | 10 g |
| water q.s.p. | 100 g |

The pH of the composition is 9.4.

At the time of use, 100 g of 20 volumes strength hydrogen peroxide are added.

This mixture, when applied for 30 minutes at 25° C. to bleached hair, imparts to the hair, after rinsing and shampooing, a very deep black-blue coloration.

EXAMPLE 12

The following dyeing composition is prepared:

| | |
|---|---|
| 2,4-diamino-butoxybenzene dihydrochloride | 0.25 g |
| para-phenylenediamine | 0.5 g |
| 2-methyl-5-N-β-hydroxyethylamino-phenol | 0.7 g |
| 2-nitro-4-methyl-6-amino-phenol | 0.70 g |
| 2-amino-3-nitro-phenol | 0.70 g |
| 3-nitro-4-N-β-hydroxyethylamino-phenol | 0.6 g |
| oleyl alcohol oxyethyleneated with two mols of ethylene oxide | 4.5 g |
| oleyl alcohol oxyethyleneated with four mols of ethylene oxide | 4.5 g |
| oleylamine oxyethyleneated with twelve mols of ethylene oxide and sold by "ARMOUR" under the name "ETHOMEEN T012" | 4.5 g |
| diethanolamides of copra fatty acids | 9 g |
| propylene glycol | 4 g |
| 2-butoxy-ethanol | 8 g |
| ethanol (of 96° strength) | 6 g |
| pentasodium salt of diethylenetriamine-pentaacetic acid | 2 g |
| thioglycolic acid | 0.5 g |
| triethanolamine | 8.5 g |
| water q.s.p. | 100 g |

The pH of the composition is 8.8.

At the time of use, 100 g of 20 volumes strength hydrogen peroxide are added.

This mixture, when applied for 20 minutes at 30° C. to hair which is naturally 90% white, imparts to the hair, after rinsing and shampooing, a red chestnut coloration.

We claim:

1. A composition suitable for dyeing human hair in the presence of an oxidizing agent selected from the group consisting of hydrogen peroxide, urea peroxide, alkaline persulfate and alkaline perborate, said composition containing at least one oxidation base and a coupling agent having the formula (I):

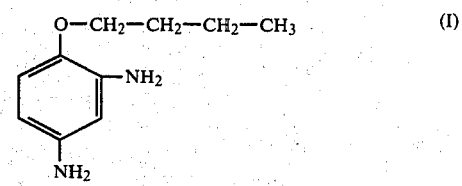

or a salt thereof.

2. A composition according to claim 1, which contains from 0.005% to 2.5% by weight, relative to the total weight of the composition, of compound of formula (I).

3. A composition according to claim 1 which has a pH from 8 to 11.5.

4. A composition according to claim 1 which also contains at least one additional coupling agent selected from the group consisting of a meta-phenylenediamine, metaaminophenol, meta-diphenol, 6-hydroxy-benzomorpholine, α-naphthol, 1-phenyl-3-methylpyrazol-5-one and 6-aminobenzomorpholine.

5. A composition according to claim 4, in which the meta-phenylenediamine is selected from the group consisting of 2,4-diamino-phenoxyethanol, 2,4-diamino-phenyl β-mesylaminoethyl ether, (2-N-carbamylmethylamino-4-amino-phenoxy)-ethanol, 2-N-β-hydroxyethylamino-4-amino-phenyl β-methoxyethyl ether, (2-N-β-hydroxyethylamino-4-amino-phenoxy)-ethanol, 2-N-β-hydroxyethylamino-4-amino-phenyl β-mesylaminoethyl ether and 2,4-diamino-phenyl β-aminoethyl ether, the meta-aminophenol is selected from the group consisting of meta-aminophenol, 2-methyl-5-amino-phenol, 2-methyl-5-N-β-hydroxyethylamino-phenol, 2-methyl-5-N-β-mesylaminoethylamino-phenol, 2-methyl-5-N-carbamylmethylamino-phenol, 3-N-carbamylmethylamino-phenol and 2,6-dimethyl-3-acetylamino-phenol, and the metadiphenol is selected from the group consisting of resorcinol and 2-methyl-resorcinol.

6. A composition according to claim 1 wherein said oxidation base is selected from the group consisting of a para-phenylenediamine, a paraaminophenol and 2,5-diaminopyridine.

7. A composition according to claim 6, in which the para-phenylenediamine is selected from the group consisting of para-phenylenediamine, 2,6-dimethyl-para-phenylenediamine, 2,3-dimethyl-para-phenylenediamine, 2,6-dimethyl-3-methoxy-para-phenylenediamine, N-β-methoxyethyl-para-phenylenediamine, N,N-di-β-hydroxyethyl-para-phenylenediamine, N-ethyl-N-β-hydroxyethyl-para-phenylenediamine, N-ethyl-N-carbamylmethyl-para-phenylenediamine, N-ethyl-N-mesylaminoethyl-paraphenylenediamine and N-β-hydroxyethyl-N-mesylaminoethyl-para-phenylenediamine, and the para-amino phenol is selected from the group consisting of para-aminophenol, 2-methyl-para-aminophenol and 3-methyl-para-aminophenol.

8. A composition according to claim 1 which contains one or both of ortho-aminophenol and pyrocatechol.

9. A composition according to claim 1 which contains 1,2,4-trihydroxy-benzene or 2,4,5-trihydroxytoluene.

10. A composition according to claim 1, which also contains at least one direct dye selected from the group consisting of ortho-nitroaniline, 2-amino-3-nitro-isopropylbenzene, 3-nitro-4-aminophenol, 3-nitro-4-N-β-hydroxyethylaminophenol, 2-methyl-4-amino-5-nitro-phenol, 2-nitro-4-methyl-6-amino-phenol, 3-nitro-6-N-β-hydroxyethylamino-anisole, 2-amino-3-nitro-phenol, (3-N-methylamino-4-nitro-phenoxy)-ethanol, (2-N-β-hydroxyethylamino-5-nitro-phenoxy)-ethanol, 3-nitro-4-N'-methylamino-N,N-di-β-hydroxyethyl-aniline, 3-nitro-4-N'-β-hydroxyethylamino-N,N-di-β-hydroxyethylaniline and 3-nitro-4-N'-methylamino-N-methyl-N-β-hydroxyethyl-aniline.

11. A composition according to claim 1, which also contains at least one alkalizing agent which is selected from the group consisting of ammonia, an alkylamine, an alkanolamine, an alkylalkanolamine, sodium hydroxide, potassium hydroxide, sodium carbonate, potassium carbonate and ammonium carbonate.

12. A composition according to claim 1, which also contains at least one acidifying agent which is selected from the group consisting of lactic acid, acetic acid, tartaric acid and phosphoric acid.

13. A composition according to claim 1, which contains from 1 to 40% by weight, relative to the total weight of the composition, of at least one organic solvent selected from the group consisting of ethanol, isopropanol, glycerol, 2-butoxy-ethanol, ethylene glycol, propylene glycol, diethylene glycol monoethyl ether and diethylene glycol monomethyl ether.

14. A composition according to claim 1, which contains from 0.05 to 1.5% by weight, relative to the total weight of the composition, of at least one antioxidant selected from the group consisting of sodium sulphite, thioglycolic acid, sodium bisulphite, ascorbic acid and hydroquinone.

15. A composition according to claim 1 to which at least one oxidizing agent has been added.

16. Process for dyeing human hair, which comprises applying thereto an effective amount of a composition as defined in claim 15 for 5 to 45 minutes, rinsing the hair, and drying it.

17. A composition suitable for dyeing human hair in the presence of at least one oxidizing agent selected from the group consisting of hydrogen peroxide and urea peroxide, comprising an aqueous solution of an effective amount of an oxidation base selected from the group consisting of (a) a paraphenylenediamine, (b) 2,5-diaminopyridine, and (c) a para-aminophenol and 0.005 to 2.5 percent by weight based on the total weight of the composition of, as a coupling agent, 2,4-diaminobutoxybenzene or a salt thereof, said composition having a pH ranging from 8 to 11.5.

18. The composition of claim 17 which also includes an effective amount of another coupling agent selected from the group consisting of (a) a meta-phenylenediamine, (b) a meta-aminophenol, (c) a meta-diphenol, and (d) one or more of 6-hydroxy-benzomorpholine, α-naphthol, 1-phenyl-3-methylpyrazol-5-one and 6-amino-benzomorpholine.

19. The composition of claim 18 wherein said another coupling agent is (a) a meta-phenylenediamine selected from the group consisting of 2,4-diaminophenoxyethanol, (2-N-carbamylmethyl-amino-4-aminophenoxy)ethanol, 2-N-β-hydroxyethylamino-4-aminophenyl β-methoxyethylether, (2-N-β-hydroxyethylamino-4-amino-phenoxy)ethanol and 2-N-β-hydroxyethylamino-4-amino-phenyl β-mesylaminoethyl ether.

20. The composition of claim 18 wherein said another coupling agent is (b) a meta-aminophenol selected from the group consisting of meta-aminophenol, 2-methyl-5-amino phenyl, 2-methyl-5-N-β-hydroxyethylaminophenol, 2-methyl-5-N-carbamylmethylaminophenyl and 3-N-carbamylmethylaminophenol.

21. The composition of claim 18 wherein said another coupling agent is (c) a meta-diphenol selected from the group consisting of resorcinol and 2-methyl-resorcinol.

22. The composition of claim 18 wherein said another coupling agent is 6-hydroxybenzomorpholine.

23. The composition of claim 18 wherein said another coupling agent is 1-phenyl-3-methyl pyrazol-5-one.

24. The composition of claim 17 which also contains a direct dye present in an amount of 0.002 to 2.5 percent by weight based on the total weight of said composition.

25. The composition of claim 24 wherein said direct dye is selected from the group consisting of 3-nitro-4-aminophenol, 3-nitro-4-N-β-hydroxyethyl-aminophenol, 2-nitro-4-methyl-6-aminophenol, 3-nitro-6-N-β-hydroxyethylamino anisole, 2-amino-3-nitrophenol, 2 nitro-3-aminophenol and 2-nitro-3-N-β-hydroxyethylamino phenol.

26. The composition of claim 17 which also contains from 0.5 to 50 percent by weight of a water-soluble surface-active agent based on the total weight of said composition.

27. The composition of claim 26 wherein said surface-active agent is present in an amount of 4 to 40 percent by weight of said composition.

28. The composition of claim 17 which also includes 1–40 percent by weight of an organic solvent to assist in solubilizing the components of said composition, said organic solvent being ethanol, isopropanol, glycerol, ethylene glycol monobutyl ether, ethylene glycol, propylene glycol, diethylene glycol monoethyl ether or diethylene glycol monomethyl ether.

29. The composition of claim 28 wherein said organic solvent is present in an amount of 5 to 30 percent by weight of said composition.

30. The composition of claim 17 which also includes from 0.5 to 5 percent by weight of a thickening agent based on the total weight of said composition.

31. The composition of claim 30 wherein said thickening agent is present in an amount of 0.5 to 3 percent by weight of said composition.

32. The composition of claim 17 which also contains from 0.05 to 1.5 percent by weight of an antioxidant.

33. The composition of claim 17 wherein said oxidation base is (a) a paraphenylene diamine selected from the group consisting of paraphenylenediamine, 2,6-dimethyl paraphenylenediamine, 2,6-dimethyl-3-methoxy paraphenylene diamine, N-β-methoxyethyl paraphenylenediamine, N,N-di-β-hydroxyethyl paraphenylenediamine, N-ethyl-N-β-hydroxyethyl paraphenylenediamine, N-ethyl-N-carbamylmethyl paraphenylenediamine and N-ethyl-N-β-mesylaminoethyl paraphenylenediamine.

34. The composition of claim 17 wherein said oxidation base is paraaminophenol or N-methyl paraaminophenol.

35. In a composition for dyeing human hair in the presence of an oxidizing agent wherein said composition contains an oxidation base and a coupling agent, the improvement comprising said coupling agent having the formula

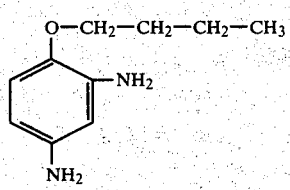
or the hydrochloride, sulfate, citrate or lactate thereof.
* * * * *